United States Patent [19]

Mercer

[11] 4,032,276

[45] June 28, 1977

[54] CAST EJECTOR

[76] Inventor: Roger W. Mercer, 1340 Arlington Drive, Fairborn, Ohio 45324

[22] Filed: Feb. 10, 1976

[21] Appl. No.: 656,916

Related U.S. Application Data

[62] Division of Ser. No. 550,109, Feb. 13, 1975, Pat. No. 3,975,489.

[52] U.S. Cl. .............................. 425/123; 425/125; 425/441; 425/451.9
[51] Int. Cl.² ...................... B29D 1/00; B29C 1/16
[58] Field of Search .......... 425/121, 123, 125, 441, 425/451.9

[56] References Cited

UNITED STATES PATENTS

| | | | |
|---|---|---|---|
| 1,526,788 | 2/1925 | Hoffman | 425/123 |
| 2,883,704 | 4/1959 | Jurgeleit | 425/123 X |
| 3,267,184 | 8/1966 | Nowicki et al. | 425/441 X |
| 3,330,006 | 7/1967 | Jenkins | 425/125 |
| 3,492,690 | 2/1970 | Goldring et al. | 425/441 X |
| 3,776,676 | 12/1973 | Kessler | 425/441 X |

Primary Examiner—Robert L. Spicer, Jr.
Attorney, Agent, or Firm—Joseph E. Rusz; Arthur R. Parker

[57] ABSTRACT

A process for forming a removable dental cast embedded with a plastic, threaded, cast ejector button, and apparatus for fabricating a plurality of cast ejector buttons comprised of a mold device including an upper plate containing a plurality of mold cavities, and a base plate incorporating coil spring means for resiliently maintaining the upper plate in a predetermined spaced-apart and open relation thereto and a plurality of rigid support elements attached, at their bottom ends, in vertically-upright relation on the base plate and slidably engaged, at their upper ends, in a bottom opening in each upper plate-mold cavity and extending in overlapping relation into the respective cavity. The upper ends of each rigid support element are threaded so that, when the mold cavities are poured with and filled by a suitable material, in the plastic flow form that is allowed to set for a specified period, a separate and internally threaded plastic cast ejector button is formed in each cavity.

1 Claim, 20 Drawing Figures

STEP 1

CAST EJECTOR

RIGHTS OF THE GOVERNMENT

There is reserved to the Government of the United States a nonexclusive, irrevocable, royalty-free license in the invention described herein with power to grant licenses for all governmental purposes.

REFERENCE TO RELATED APPLICATIONS

This is a division of application Ser. No. 550,109, filed Feb. 13, 1975, now U.S. Pat. No. 3,975,489 Feb. 13, 1975.

BACKGROUND OF THE INVENTION

This invention relates generally to the field of cast removable partial dentures and, in particular, to an improved technique for removing a master dental cast from an impression material-containing, duplication flask.

Laboratory techniques used in the fabrication of partial dental casts are generally accomplished by means of a reversible hydrocolloid impression material. Naturally, when a partial denture is indicated, the dentist will first have a negative impression of the oral cavity made by the insertion in the patient's mouth of a dental impression tray. The negative impression thus made is poured with a suitable dental stone material and allowed to set a specified time to thereby produce a positive impression that may be used as a master dental cast. Thereafter, by placing this master cast in a duplicating flask and filling with a suitable hydrocolloid material, for example, a new negative impression duplicating the previously obtained impression of the oral cavity now found in the master cast may be achieved.

Under present methods, the master dental cast is removed from the hydrocolloid impression material in the duplicating flask by any of several means to include the use of a pair of sharp instruments or, in some cases, even the fingers of the human hand to grip the cast in an oppositely-disposed relation around the circumference thereof to thus lift the cast from the impression material. With such techniques, however, it is practically impossible to remove the dental cast without imposing some adverse stresses on the impression material. It is known that such adverse stresses result in an inacurate cast and, although dentists, dental laboratory technicians and patients have been forced to live with this situation for the want of a better solution, it is quite evident that such a situation is not a desirable one. This led to the development of the novel means of the present invention which, as will readily appear hereinafter in the following summary and detailed description, solves or substantially solves the aforementioned problem of adverse stress in a new, improved and yet relatively simplified manner.

SUMMARY OF THE INVENTION

The present invention consists in the embedding of an internally threaded, plastic ejector button in a flush relation within the dental stone constituting the positive impression or master dental cast being produced from the pouring of an appropriate material, in a plastic flow state, in the initial negative impression made from the insertion of a dental impression tray in the patient's oral cavity. The internal thread characteristic of the plastic ejector button enables the insertion therein of an externally threaded handle member which, at the time the dental cast is to be duplicated and the removed from an impression material in a duplicating flask, is thereby screwed into the opening in the cast ejector button. In this manner, a two-fold purpose is served; namely, the removal of the cast from the impression in a greatly facilitated manner and the substantial absence of any adverse stresses being applied to the impression material during such removal.

The foregoing inventive technique also involves the use of a novel mold apparatus for simultaneously or substantially simultaneously fabricating a plurality of the above-noted threaded, plastic, cast ejector buttons for their use with one each being embedded in a dental cast. Said mold includes a base plate having a plurality of vertically-upright support elements mounted thereon, an upper plate having a plurality of relatively enlarged, mold cavities distributed along the upper surface thereof and with each mold cavity having a relatively small opening at the bottom surface thereof that slidably receives in upward overlapping thereof a corresponding one of the said base plate-supported-vertically-upright support elements. A set of oppositely-disposed coil springs mounted on the base plate adjacent or substantially adjacent opposite ends thereof and disposed in resilient contact between said base and upper plates provides for the resilient support of said upper plate is a predetermined spaced apart relation and open position relative to the base plate. For this purpose, the aforesaid plurality of vertically upright support elements mounted on the base plate each incorporates a centrally-disposed, non-threaded portion that is in an actual, relatively snug-fit and slidable relation with the relatively small, bottom opening of each of the relatively enlarged, mold cavities disposed along the top surface of the upper plate. In addition, the upper end of each vertically upright support element incorporates a threaded portion that is centered in the appropriate relatively enlarged mold cavity and which always remains clear of the respective bottom surface-relatively small opening that slidably engages the centrally-disposed, non-threaded portion of the corresponding vertically upright support element.

To fabricate the previously-referred to plurality of threaded, plastic ejector buttons, an appropriate amount of material in the plastic flow state is poured into and completely fills each of the upper plate-relatively enlarged mold cavities with the said material either completely enclosing the upper threaded end of a respective base plate-mounted-vertically-upright support element, or the said threaded end could extend further upwardly into the mold cavity so as to thereby form a complete threaded opening through the plastic ejector button. In this manner, each plastic button thereby cast is formed with an internally threaded opening. After setting for the required time to harden into the finished product, the mold may then be placed in a suitable clamp device and the upper plate thus moved downwardly to a closed position with the base plate to thereby now fully expose the plurality of now-formed ejector buttons. The latter may now be easily, quickly and individually removed by the simple manual unscrewing thereof from the upper, threaded end portion of the corresponding vertically-upright support element mounted on the base plate. In this manner, a stockpile of cast ejector buttons may be quickly fabricated for future use.

When it is desired to produce a partial denture and after the dental impression tray has been utilized to produce an accurate negative impression of the patient's oral cavity, the dental lab technician then pours the negative impression previously made in the said impression tray to thereby produce a positive impression that may be used as the master dental cast of the particular patient's oral cavity. However, in the case of the instant invention being applied thereto, a plastic, threaded ejector button previously fabricated by the use of the aforementioned mold is incorporated into a base portion of the dental stone constituting the master dental cast after the pouring of the latter into the negative impression, as noted above. For this purpose, a new and improved process for accomplishing the aforenamed cast ejector button-incorporation in the dental stone will be further described hereinbelow. After incorporating the cast ejector button in the dental stone comprising the master cast, the latter is placed face up on the inside of a bottom cover element of a duplicating flask member having a pouring spout on its top side and a supply of a reversible hydrocolloid material is admitted, naturally in the plastic flow form, through the pouring spout into and, is made to fill the interior of the flask in completely surrounding relation to the master cast. After being allowed to set for a specified period, a new negative impression is thereby formed in the hydrocolloid material. The flask is next turned over, the bottom cover removed and the master cast extracted from the hydrocolloid impression material. To accomplish the latter feature in the unique manner of the present invention, a handle member is quickly and easily screwed into the externally threaded opening in the cast ejector button previously built into the base portion of the master dental cast during the formation of the latter, and the said cast is then lifted from the impression material with a single straight out movement without damaging the impression material.

Other objects and unique advantages of the invention will become self-evident hereinafter from the following disclosure, taken in connection with the accompanying drawings, in which:

DESCRIPTION OF THE PREFERRED EMBODIMENT

Figure 1:
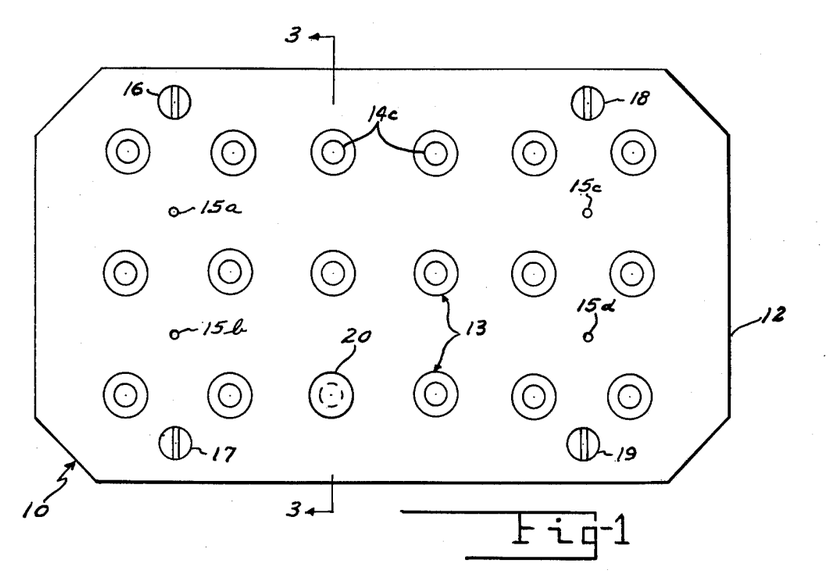
FIG. 1 is a top view of the new and improved plastic, threaded, dental cast ejector button-making, mold device of the present invention, illustrating one arrangement of a plurality of mold cavities disposed along and within the top plate surface thereof.
Figure 2:
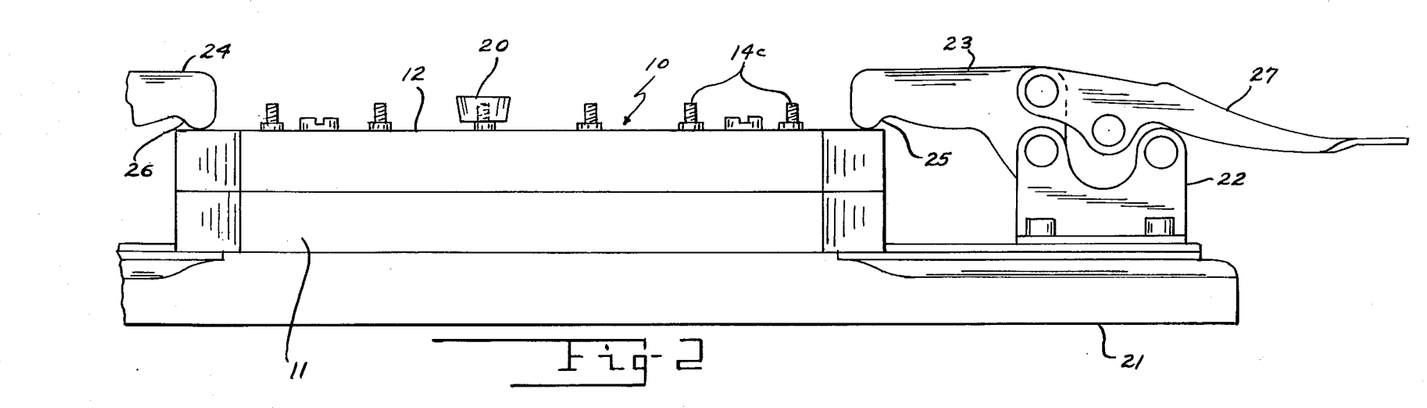
FIG. 2 is a side view, partly broken-away, illustrating the mold device of FIG. 1 in its closed position after being placed in a clamp device.
Figure 3:
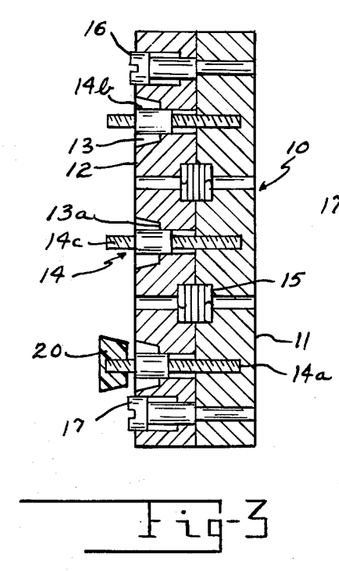
FIG. 3 is a cross-sectional view, taken about on line 3—3 of FIG. 1, showing details of the interconnection between the upper and base plate elements of the inventive mold device when the latter is in its closed position of FIG. 2.
Figure 4:
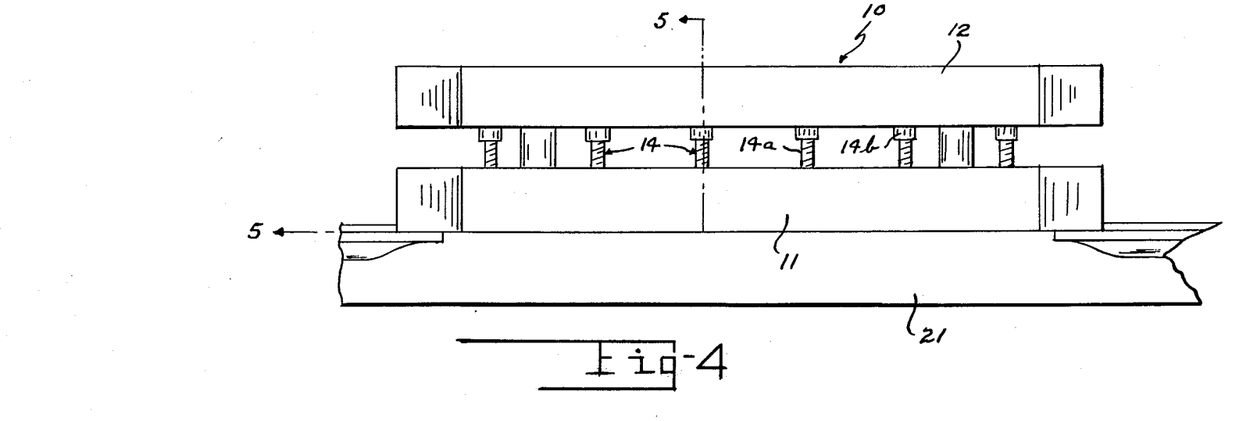
FIG. 4 is a second side view, partly broken-away and somewhat similar to that of FIG. 2 but showing the inventive mold device in its normally open position.
Figure 5:
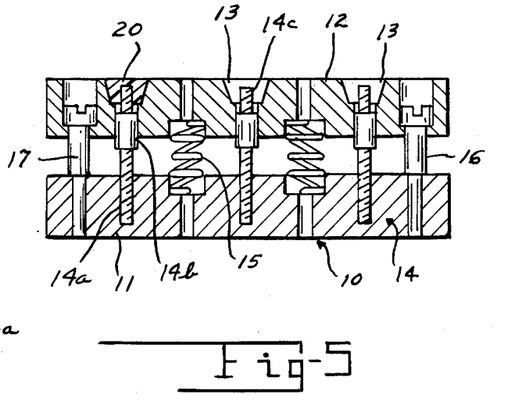
FIG. 5 is another cross-sectional view, taken about on line 5—5 of FIG. 4 and showing further details of the interconnection between the upper and base plate elements of the novel mold device of the invention when in its normally open position.

Referring generally to the drawings and, in particular, to FIG. 2 thereof, the new and improved mold device used to fabricate a plurality of the plastic, threaded, dental cast ejector buttons of the present invention is indicated generally at 10 as principally including an aluminum base plate 11, an aluminum top plate 12 incorporating a plurality of cast ejector button-making, mold cavities, as at 13 (FIG. 1) and interconnecting means as indicated generally at 14 and 15 particularly in FIGS. 3, 4 and 5, for both slidably and resiliently positioning the top plate 12 relative to the base plate 11, as will more readily appear hereinafter.

As is seen more clearly in the aforementioned FIG. 5, for example, interconnecting means 15 actually constitutes a resilient support arrangement consisting of coil springs disposed preferably with a pair of such springs located on or substantially adjacent opposite ends of the base and top plates 11 and 12. The anchor points for the upper or top ends of the springs 15 that are disposed in the top plate 12 may be seen respectively at 15a, 15b, 15c and 15d in FIG. 1. Naturally, similar and aligned anchored points are used in the base plate 11. Again referring to the said FIG. 5, these coil springs 15 are automatically operative to normally retain the top plate 12 in a spaced-apart relation over the base plate 11 or, in other words, in its open position. On the other hand, the interconnecting means 14 constitutes rigid support elements which incorporate a lower, threaded support portion 14a for fixed attachment in the base plate 11, a centrallydisposed, non-threaded support portion 14b and a threaded top support portion 14c. The non-threaded, central portion 14b, which is slightly larger in diameter than the other portions 14a, 14c, is utilized to provide specifically for the slidable, though relatively snug-fit, relation of each of said rigid support elements 14 in a narrowed opening 13a formed in the bottom of each of the mold cavities 13 and extending through the wall surface or thickness of the top plate 12. With this unique arrangement, therefore, the top plate 12 may be rather easily repositioned between its open position of FIGS. 4 and 5, relative to the base plate 11, and its closed position of FIGS. 2 and 3, the latter operation being effected by clamp means to be further described hereinbelow.

When it is desired to produce a supply of the plastic, threaded, dental cast ejector buttons of the invention, a plurality of such buttons, which may be preferably made of an acrylic material, are poured, in the plastic flow form, in each of the series of mold cavities 13 (FIG. 1) to completely fill the appropriate cavity and entirely enclose the top threaded portion 14c of a corresponding support element 14, which threaded portion 14c normally extends upwardly into the particular mold cavity 13. As an alternative, the upper threaded end 14c of each support element 14 could extend further upwardly into the respective mold cavity 13 to thereby form the finished ejector button 20 with a complete opening, if desired. At this time, of course, the top plate 12 is being held in its upward or open position, illustrated in FIGS. 4 and 5, relative to the base plate 11, by the normal action of the coil springs 15. In this connection, to prevent the complete separation between the base and top plates 11 and 12, the mold device is equipped with a pair of main, plate connecting screws, indicated respectively at 16, 17, 18 and 19 in FIG. 1, for example, which are disposed in corresponding pairs on or adjacent the opposite ends of the mold device 10, as is clearly illustrated.

After being allowed to set for at least twenty minutes in a pressure pot and while immersed in hot tap water, each of the plastic, cast ejector buttons, one of which is shown at 20, is now ready for removal from the hold device 10. Of course, at this time, said ejector buttons, as at 20, now incorporate an internally-threaded opening because of the central disposition of the respective threaded top support portion 14c within the corresponding mold cavity 13. In this regard, it is to be noted that the said threaded top support portion 14c, as is specifically illustrated in FIG. 5, terminates at a point within the mold cavity 13 just below a flush relation with the entrance to said cavity. In this manner, the internally threaded opening of the respective plastic ejector button, as at 20, is naturally formed with a closed end at its bottom surface. Also, in actual practice, each mold cavity, as at 13, may be specifically configured to give, for example, a 4-degree taper to the cast ejector button, as at 20, for an express purpose to be further set forth. To remove each of said plurality of ejector buttons, as at 20, the mold device 10 may be mounted in any appropriate clamp device, the base portion of which being indicated at 21 in FIGS. 2 and 4. As seen in FIG. 2, mounted on the said clamp-base portion 21 by the suitable vertically upright clamp-mounts, as at 22, are the pair of clamps at 23 and 24. Said clamps 23, 24 are specifically spaced-apart, relative to each other, a predetermined distance that is expressly tailored to the length of the mold device 10, so that when the latter is placed in centered relation on top of the base portion 21, the opposite ends of the said mold device 10 are in correct position to be securely clamped downwardly against the base portion 21 by the oppositely-disposed jaws 25 and 26 of the clamps 23 and 24 when the latter are respectively and preferably simultaneously operated to such position by the manual operation of the clamp actuating arms or levers, as at 27 (FIG. 2). The above-described clamping operation of the clamp device actually, of course, repositions the normally-open position of the top plate 12 downwardly into its closed position in clamping relation against the base plate 11. This downward movement of the top plate 12 to its closed position has the natural effect of automatically lowering each mold cavity, as at 13, disposed in the upper surface of the top plate 12, and thereby simultaneously extracting the now hardened and thus fully formed plurality of plastic ejector buttons, as at 20, from their respective mold cavity 13. The net result of the foregoing operation is to fully expose the respective ejector button 20 to view above the surface of the top plate 12. It then only remains to manually remove each button, as at 20, by its relatively easy and rapid unscrewing from the respective threaded top support portion 14c of the corresponding support element 14.

Figures 10, 11:
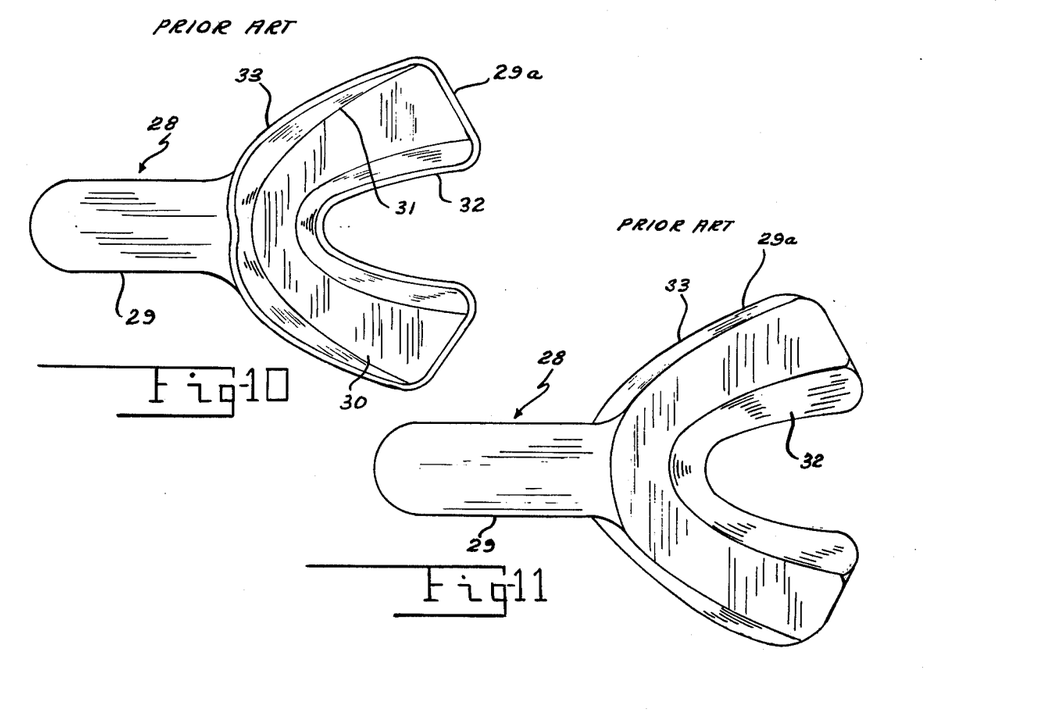
FIGS. 10 and 11 are respectively top and bottom plan views of a typical lower dental impression tray.

In accordance with the novel teachings of the present invention, a threaded, plastic ejector button, fabricated in the manner indicated hereinbefore by the use of the inventive mold device 10 of FIGS. 1–5, may be uniquely incorporated in the dental stone comprising a master dental cast used to produce a partial denture at the time the negative impression of the patient's oral cavity is being poured with an appropriate material used for this purpose. This whole process is initiated when a conventional type of dental impression tray device, indicated generally at 28 in the top view of FIG. 10 and in the bottom view of FIG. 11, is inserted into the mouth of the patient to obtain a negative impression of the oral cavity. To this end, the dentist grips the handle portion, at 29, and positions the main tray portion 29a within the oral cavity. For this purpose, the bottom surface and side walls, which are upright and indicated at 32 and 33, of the said tray portion 29a are preferably lined with integral portions of a layer of a suitable irreversible hydrocolloid impression material, as at 30 and 31.

Immediately after the impression of the oral cavity is taken with the use of the dental impression tray device, as at 28, which operation actually gives a so-called "negative" impression, the latter should be poured (filled) with a gypsum-like material, such as plaster or stone to thereby produce a positive impression or, in other words, to produce a master dental stone cast of the oral cavity. The finished product of the latter member is actually accomplished after allowing a setting time of 45 minutes. It is during this stage; that is, immediately after the pouring of the dental stone into the previously obtained negative impression, that the new and improved technique of incorporating the previously-fabricated plastic, threaded, dental cast ejector button, as at 20, into the said dental stone is accomplished in the new and novel and yet relatively simplified process set forth hereinafter.

Figure 12:
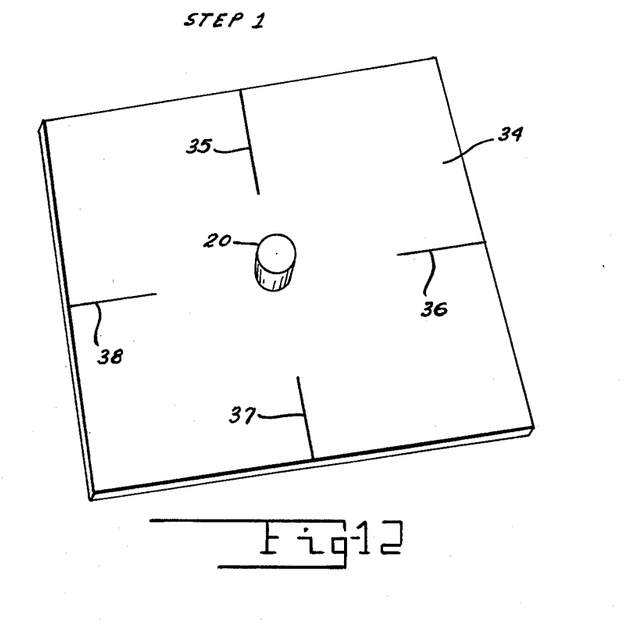
FIGS. 12 through 17 respectively depict in schematic form the various steps used in the new and improved process of embedding a plastic, threaded, dental cast ejector button in the base portion of the dental stone comprising the removable master dental cast of the invention.
Figures 13, 14, 15:
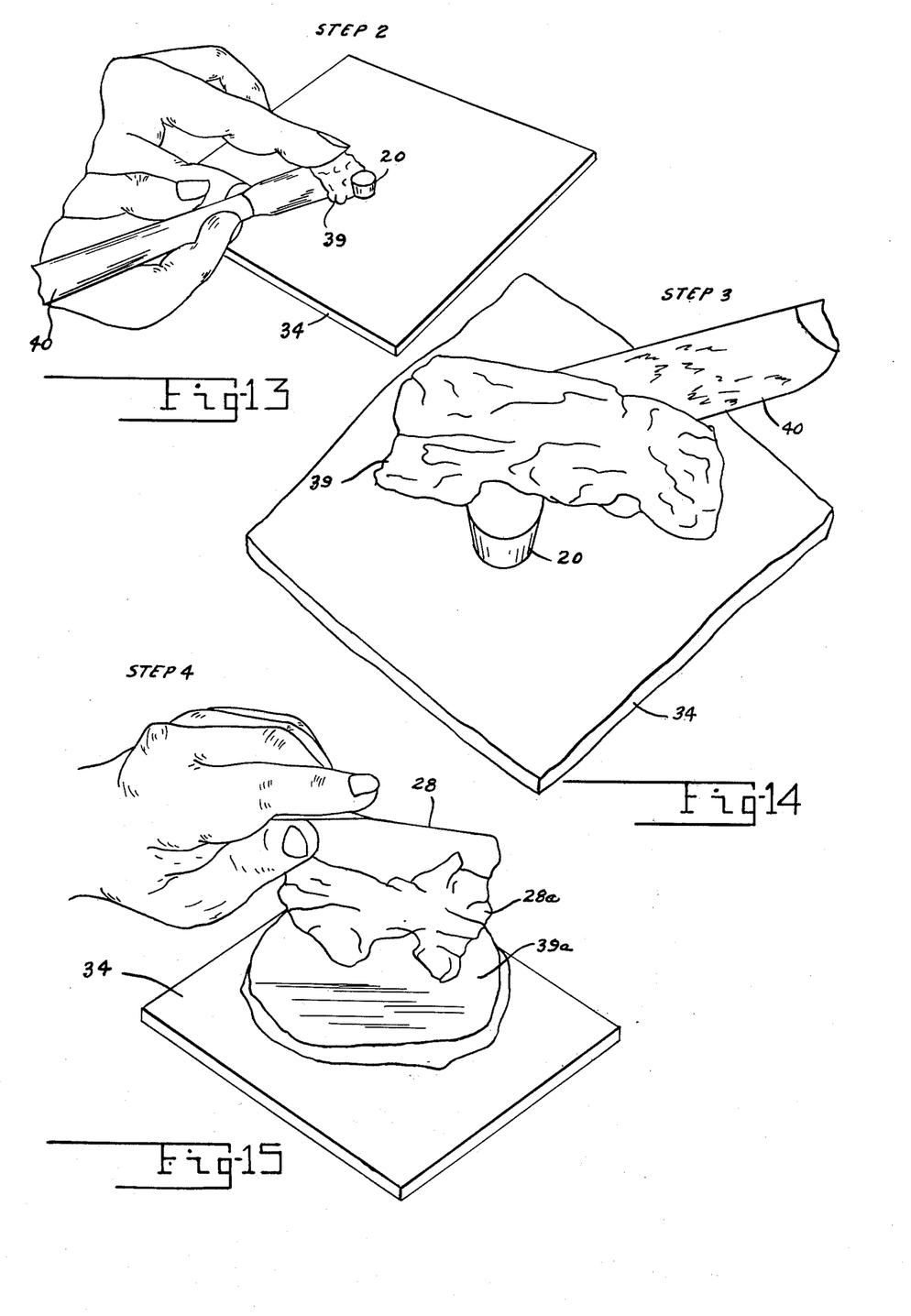
Figure 16:
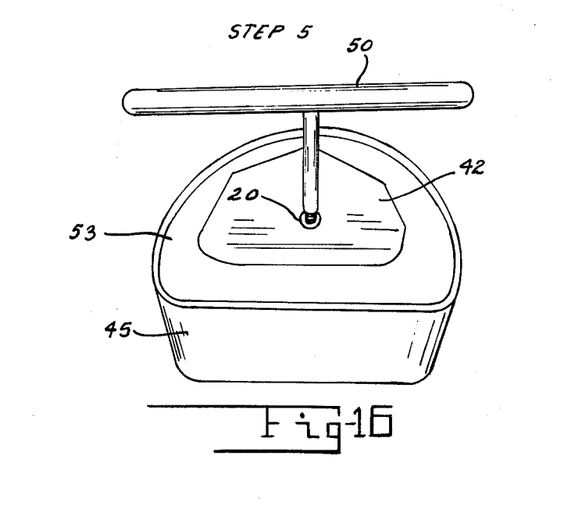

Initially, to install the inventive cast ejector button 20 in the dental stone, the said cast ejector button 20 is first placed onto the top of a plastic slab, indicated at 34 in FIG. 12. This is step No. 1 of the inventive process and consists simply of screwing the internally threaded button 20 in position on a screw (now shown) incorporated in a centered relation on the said slab 34. In this connection, as a mechanical expedient means of centering the screw on the slab 34, the centering markers, indicated at 35, 36, 37 and 38 may be used and then removed once the screw is installed. In step No. 2, depicted in FIG. 13, the dental lab technician begins to adapt the dental stone, indicated at 39 as being applied by any suitable instrument, such as a butter knife at 40, around the ejector button 20. This must be done very carefully to ensure that there are no voids between the plastic of both the ejector button 20, and the slab 34, and the dental stone itself. In step Nos. 3 and 4 of FIGS. 14 and 15, respectively, the process is continued whereby the dental stone 39 (FIG. 14) is further built up by the use of said instrument 40 to form a dental stone base at 39a (FIG. 15) which now has completely covered the ejector button 20. In the aforesaid step No. 4 of FIG. 15, the now-poured negative impression-containing, dental tray device 29, which has been setting for approximately five minutes, is now turned upside down and dental stone 29a material thereof is carefully worked into the initially formed dental stone base at 39a so that a substantial dental stone base of a sufficient size to retain the inventive cast ejector button, as at 20, therewithin is formed and to accommodate the particular oral cavity. The said dental stone 28a is thoroughly worked into, and mixed with the originally formed dental stone base 39a now completely covering the cast ejector button 20 to thereby collectively provide the requisite built up of the master dental cast base, seen in its completed form at 42, for example, in FIG. 16.

Once the above-described dental cast base, along with the complete cast, has been allowed to set the required time, which, in this case, is the previously-referred to 45 minutes, the plastic slab 34, used in the preparation of the now-ejector button-embedded, dental cast-base 42, is removed by simply unscrewing from the said button 20, and the dental impression tray device 28 is carefully removed from the completed and now-hardened cast 42. Of course, suitable instruments, such as knives, are used to appropriately trim the edges of the base 42 and to place it into the final desired configuration for its further use in the step No. 5 of FIG. 16 to be explained below.

Figure 6:
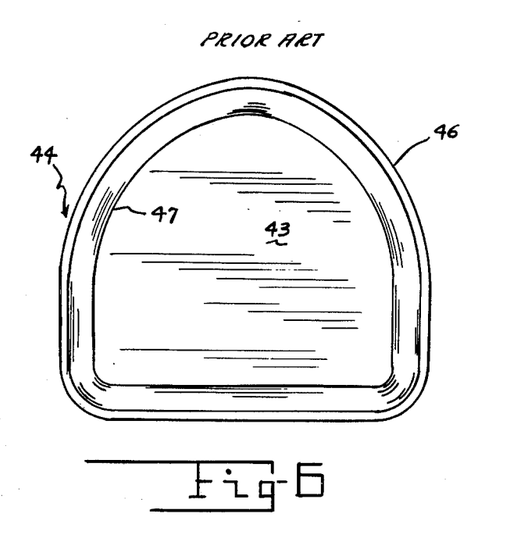
FIGS. 6 and 7 are plan and side views, respectively, of the bottom cover plate element used with the duplicating flask involved with the new and improved impression-duplicating and dental cast removal process of the present invention.
Figure 7:
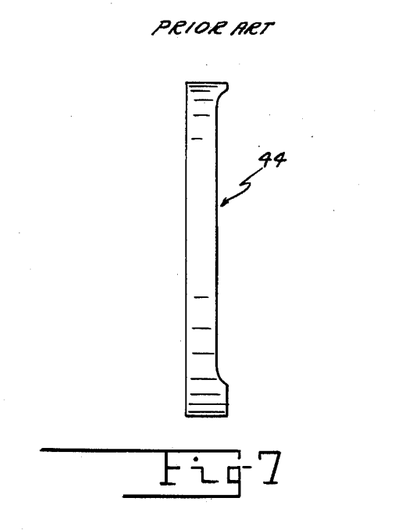

In preparation for the above-referred to step No. 5 in the inventive process, the now-finally shaped and formed master dental cast 42 (FIG. 5), which has been fabricated, as outlined hereinabove, with the inventive ejector button 20 embedded in the base 39 thereof, is placed in centered relation on the bottom inside surface 43 of a cover plate or lid, seen at 44 in the plan and side views thereof in FIGS. 6 and 7, of a duplicating mold or flask, indicated generally at 45 in the top plan and side views thereof depicted in FIGS. 8 and 9. In this regard, it is noted that the bottom inside surface 43 of the cover plate or lid 44 incorporates an inside, raised circumferential portion 47 and an upwardly projecting side portion at 46 that is raised further upwardly of the inside, raised circumferential portion 47. With this arrangement, after placing the master dental cast 42 on the said bottom inside surface of the said cover plate of lid 44, the duplicating flask 45 may then be placed in position on top of the lid 44 with its circumference, at 48 (Note FIG. 9) resting on the inside raised circumferential portion 47 formed on the bottom surface 43 of the said lid 44 and being further positioned just inside of the raised side portion 46 thereof.

Figure 8:
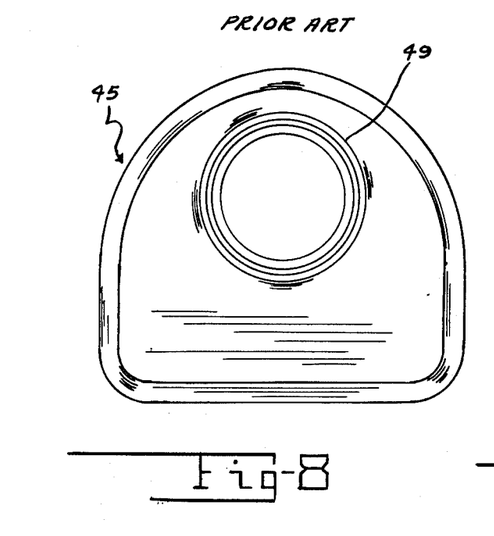
FIGS. 8 and 9 respectively depict top and side views of the main duplicating flask member used with the bottom cover plate element of FIGS. 6 and 7.
Figure 9:
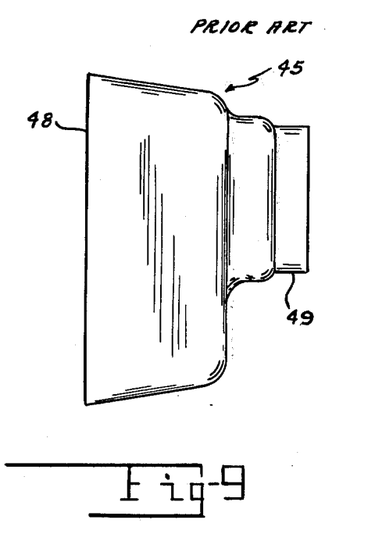

After placing the master dental cast 42 on the lid 44 and covering the same with the duplicating flask 45, the latter may be completely filled with a reversible hydrocolloid impression material by the injection thereof, in the plastic flow form, through a pouring spout 49 formed on top of the duplicating flask 45 (see FIGS. 8 and 9). This complete filling of the inside space enclosed by the duplicating flask 45 and, of course, surrounding the master dental cast 42 positioned therewithin results in the production or duplication of the said master dental cast 42 in a conventional manner to form a new negative impression thereof after, of course, the injected hydrocolloid material, indicated at 53 in FIG. 16, for example, is allowed to set for a specified and known period for the particular material.

Figure 17:
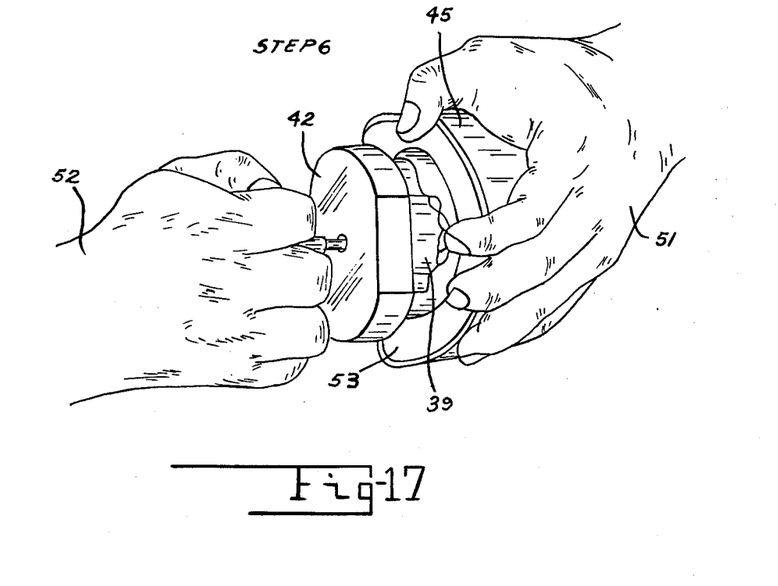

Upon the passing of the required setting time for the reversible hydrocolloid material injected into the duplicating flask 45, step No. 5 in the new and improved process of the present invention proceeds by the screwing of an externally threaded portion of a handle member 50 (FIG. 16) into the internally threaded opening previously cast into the plastic, threaded cast ejector button 20. The removal of the master dental cast 42 is then accomplished by holding the hydrocolloid material-containing duplicating flask or mold 45 in the left hand 51 for a right-handed person, as is illustrated in the step No. 6 view of FIG. 17, and by grasping the said handle member 50 in the right hand 52, the master dental cast 42 is rather easily and quickly removed by a quick snap outwardly in a straight and horizontal direction, without placing any of the adverse stresses on the hydrocolloid material 53 with the resulting inaccuracies being thereby applied to the negative dental impression found with the use of other dental cast removal techniques in current vogue.

Figure 18:
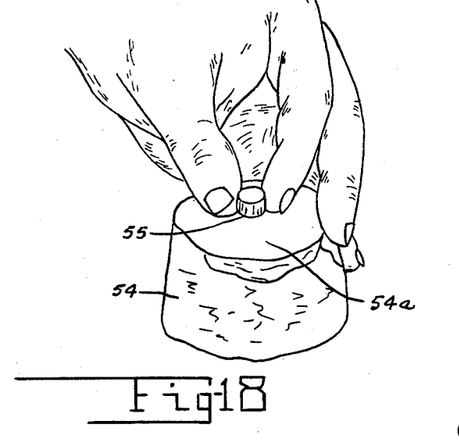
FIG. 18 schematically shows an alternate means of embedding the novel plastic button of the invention in the master castdental stone.

As an alternative technique, shown in the schematic of FIG. 18, the dental impression tray, after, of course, having been inserted in the patient's oral cavity to obtain a negative impression, may be entirely enclosed, except for the allowance of a top opening, by the use of a so-called boxing wax material, indicated generally at the reference numeral 54. Again, as described hereinabove, the requisite master dental cast is produced by pouring a gypsum-like material naturally in the plastic flow form into the top open end of the now-boxed negative impression-containing, dental impression tray. Thereafter, the plastic, threaded cast ejector button as at 55 in the aforementioned FIG. 18 may be manually embedded in the bed or base portion 54a of the dental stone material and, again, the cast is allowed to set for the previously-noted 45 minute period.

Figure 19:
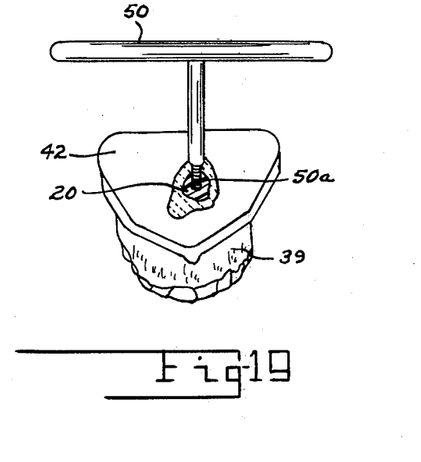
FIG. 19 is a somewhat schematic and top perspective view of the master dental cast with the cast removal handle shown installed in the plastic button embedded therein and after the cast has been removed from the duplicating flask of FIG. 20 by the use of said handle.
Figure 20:
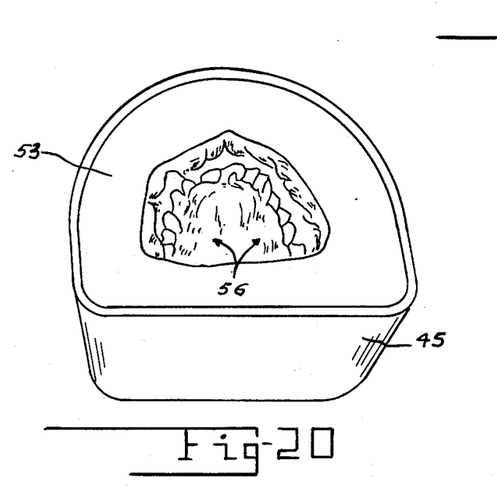
FIG. 20 is another somewhat schematic top perspective view of the reversible hydrocolloid impression shown disposed in the duplicating flask after the master dental cast has been removed therefrom.

Referring specifically to FIGS. 19 and 20, the now-removed master dental cast and separate duplicating flask are shown respectively at 39 and 45. The base portion 42 (FIG. 19) of the separate master dental cast has been partly broken away to more clearly disclose the depth to which the threaded portion 50a of the handle member 50 may be preferably adjusted within the internally threaded opening in the ejector button 20. Another important characteristic of the said ejector button 20, one that has already been mentioned hereinbefore, is positively illustrated; namely, the 4 degree taper that has been built into the said button 20. This tapered configuration, which as is clearly shown in the said FIG. 19 provides the wider button-diameter at its inner, bottom end, ensures a positive hold between the button and the base portion 42 of the master dental cast 39 that is considerably stronger than would be the case without the taper. In this manner, reasonable assurance is inherently built into the present invention against any separation occurring between the plastic button 20 and the handle member 50 when, of course, the latter is being used to remove the cast 39 from the hydrocolloid material. Of course, as previously described, after the removal of the master dental cast 39 from the duplicating flask 45, a negative impression, as seen more clearly and generally at 56 in the aforementioned FIG. 20, is left in the hydrocolloid material 53 contained within the said duplicating flask 45. It then only remains the conventional step of pouring the negative impression 56, again, with a suitable, gypsum-like material, for example, to thereby make a positive impression-copy of the master dental cast for the subsequent use thereof by the dentist or dental lab technician in fitting a partial denture, for example, to the particular patient.

Thus, a new and improved apparatus for producing a plastic, threaded cast ejector button, and improved and yet simplified process for incorporating the said ejector button in the dental stone comprising the master dental cast of a partial denture during the pouring of the negative impression of the oral cavity has been developed by the present invention. Moreover, by enabling the dental lab technicial to firmly and manually hold the negative impression in the duplicating flask in one hand while simultaneously removing the master dental cast with the other hand grasping a handle member screwed into the embedded cast ejector button, the new and improved dental cast technique of the inventive method offers significant advantage over the previously used technique of using either the fingers or a pair of sharp instruments to pry the cast loose from the negative impression, which prior techniques result in the marring of or damage to the said negative impression and even sometimes causes the disasterous separation of the impression material from the duplicating flask during the cast removal step.

Although the foregoing description was had with specific reference to the fabrication of partial dentures, it is to be understood that the inventive ejector button-casting apparatus and process for incorporating the ejector button in the cast during the pouring of the negative impression is clearly of more general utility and could, therefore, be equally applicable for use with other molded or cast articles both in the dental and other fields without departing from the true spirit or scope of the invention.

I claim:

1. Apparatus for casting one or more articles, such as a plastic, threaded dental cast ejector button, each with an internally threaded opening and comprising; a mold device having a flat plate member means including a movably-mounted, top plate member incorporating one or more mold cavities for receiving therein the material to be cast in a plastic flow form; a fixedly-mounted, base plate member mounting an externally-threaded, rigid support and mold-modifying rod element for each of said mold cavities and disposed in adjustable and removably-mounted relation on said base plate member below said top plate member and each having a vertically-oriented top rod end portion extending into and projecting upwardly through a centrally disposed opening in the bottom of each of said mold cavities formed in said top plate member; first, resilient interconnecting means disposed between said fixed base plate member and said movable top plate member, and normally holding said top plate member in an upper, spaced-apart relation and open position relative to said base plate member; second, rigid interconnecting means constituting said rod members and each incorporating a first, lower, threaded rod end portion fixed and threadedly enlarged in vertically-upright relation to and on said base plate member to thereby provide the said adjustable and removably-mounted relation thereto, a second, centrally-disposed, non-threaded rod portion enlarged to be slidably engaged in relatively snug-fit relation in the said bottom opening in each of said mold cavities, and a third, upper, threaded, rod end constituting the said top rod end portion normally disposed in substantially centered relation within the respective mold cavity when said top plate member is in the said upper open position relative to said base plate member to thereby form the said internally threaded opening in each of said casted articles; and manually-controlled means comprising a hand-operated clamping device for repositioning said top plate member downwardly into a closed position against said base plate member to thereby automatically remove each of said casted articles from the respective mold cavity and simultaneously completely expose it to view above the mold cavity for its subsequent manual removal by the unscrewing thereof from the respective third, upper, threaded, rod end portion.

* * * * *

UNITED STATES PATENT OFFICE
CERTIFICATE OF CORRECTION

PATENT NO. : 4,032,276
DATED : June 28, 1977
INVENTOR(S) : Roger W. Mercer

It is certified that error appears in the above-identified patent and that said Letters Patent are hereby corrected as shown below:

Column 1, lines 12 and 13, cancel "Feb. 13, 1975", second occurrence.

Column 1, line 47, "inacurate" should read --- inaccurate ---.

Column 1, line 69, "the", second occurrence, should read --- then ---.

Column 6, line 58, "now" should read --- not ---.

Column 10, line 21, for the claim, "enlarged" should read --- engaged ---.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks